United States Patent
Clark

(10) Patent No.: US 6,265,883 B1
(45) Date of Patent: Jul. 24, 2001

(54) APPARATUS AND METHOD FOR COMBINING MEASUREMENT OF ELECTRICAL PROPERTIES AND DEPTH OF A FLUID

(76) Inventor: Lloyd Douglas Clark, 15 Conrad St., San Francisco, CA (US) 94131

(*) Notice: Subject to any disclaimer, the term of this patent is extended or adjusted under 35 U.S.C. 154(b) by 317 days.

(21) Appl. No.: 08/810,477

(22) Filed: Mar. 1, 1997

(51) Int. Cl.[7] .................................................. G01R 27/08
(52) U.S. Cl. ............................................................ 324/713
(58) Field of Search .................................... 324/713, 523, 324/509; 219/133

(56) References Cited

U.S. PATENT DOCUMENTS

| | | | |
|---|---|---|---|
| 4,021,730 | 5/1977 | Brinegar | 324/523 |
| 4,293,756 | 10/1981 | Hoyt | 219/133 |

OTHER PUBLICATIONS

"Operator's Manual, Conductivity Meter Model 427" Scientifica, 340 Wall St., Princeton, NJ 08540.*

Level measurement section from catalog, pp. K–5 to K–14 Omega Engineering, Inc., 1 Omega Dr., Stamford, CT 06907 vol. 29, Book 2 "Handbook and Encyclopedia", 1995.*

* cited by examiner

Primary Examiner—Safet Metjahic
Assistant Examiner—Etienne LeRoux

(57) ABSTRACT

An assembly of probes (1000) measures both the electrical properties and the depth of a fluid (1045). A first probe section (1040) is electrically energized, while a second probe section (1030) is de-energized. In a first measurement, the electrical properties of the fluid are measured. Low- and high-frequency, alternating potentials are used in measuring the conductivity and dielectric constant of the fluid. These potentials cause a current to flow in the fluid and also in a proximate conductor (1010), which is connected to the input of an operational amplifier (1080). The operational amplifier converts the current to a voltage whose amplitude and phase are measured using a precision rectifier (1092), a voltmeter (1096) and an oscilloscope (1094) (or alternatively with an analog-to-digital converter (1100), and a microprocessor (1150)). A similar measurement is made with a second probe section (1030) also energized. The electrical properties of the fluid (1045) previously determined are then used in combination with a second current measurement and knowledge of the geometry of the second probe (1030) to determine the depth of immersion of both probes in the fluid.

24 Claims, 7 Drawing Sheets

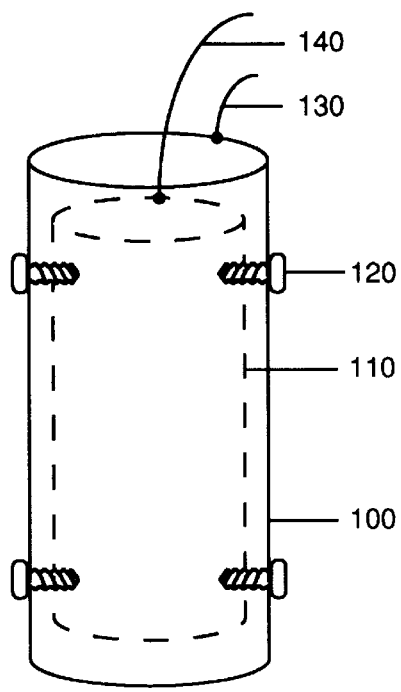
Fig. 1
PRIOR ART
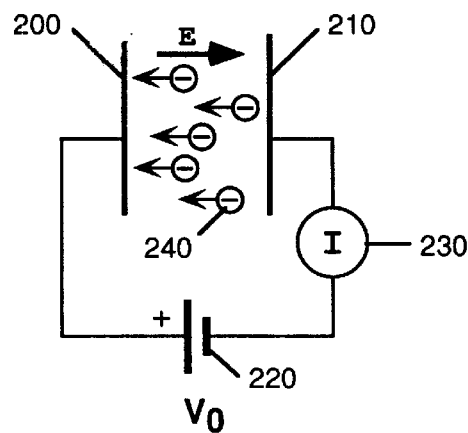
Fig. 2 PRIOR ART. t = 0⁺
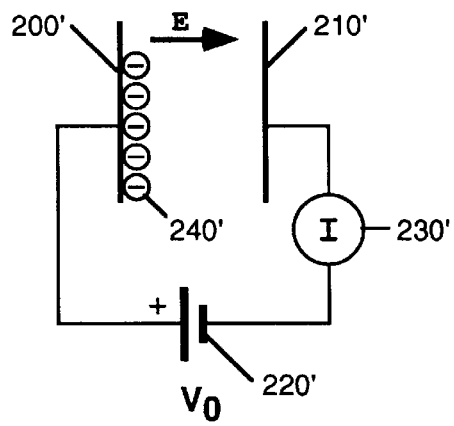
Fig. 3 PRIOR ART.
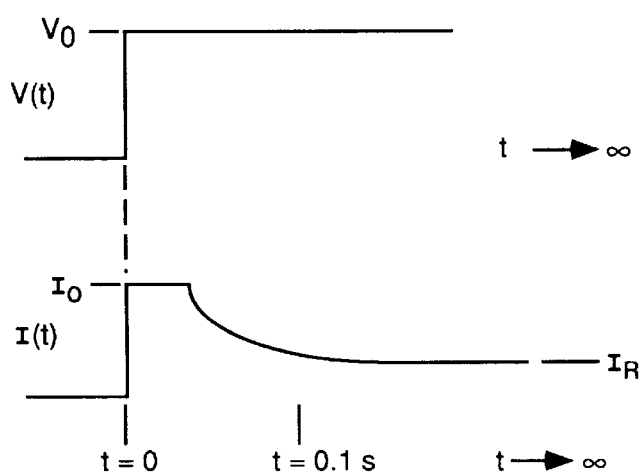
Fig. 4. PRIOR ART.

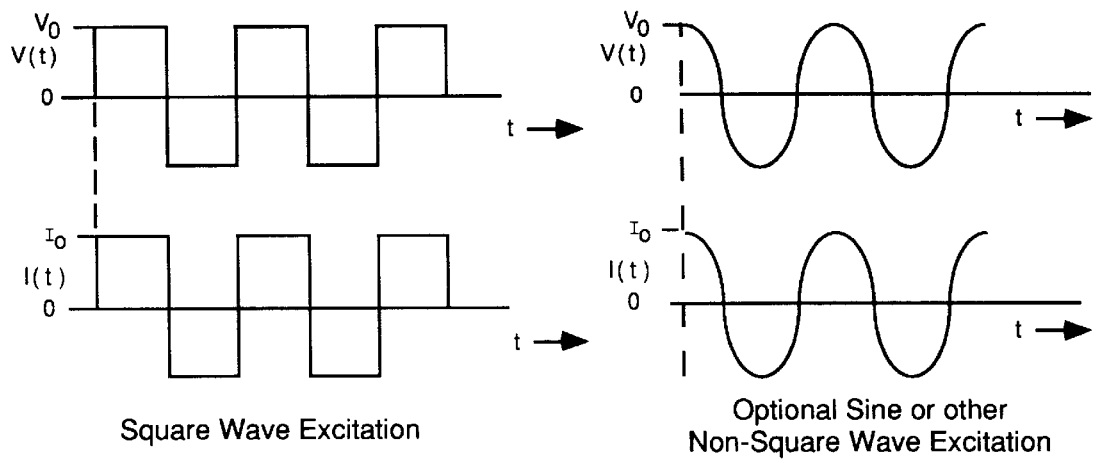
Fig. 5 PRIOR ART—Low Frequency
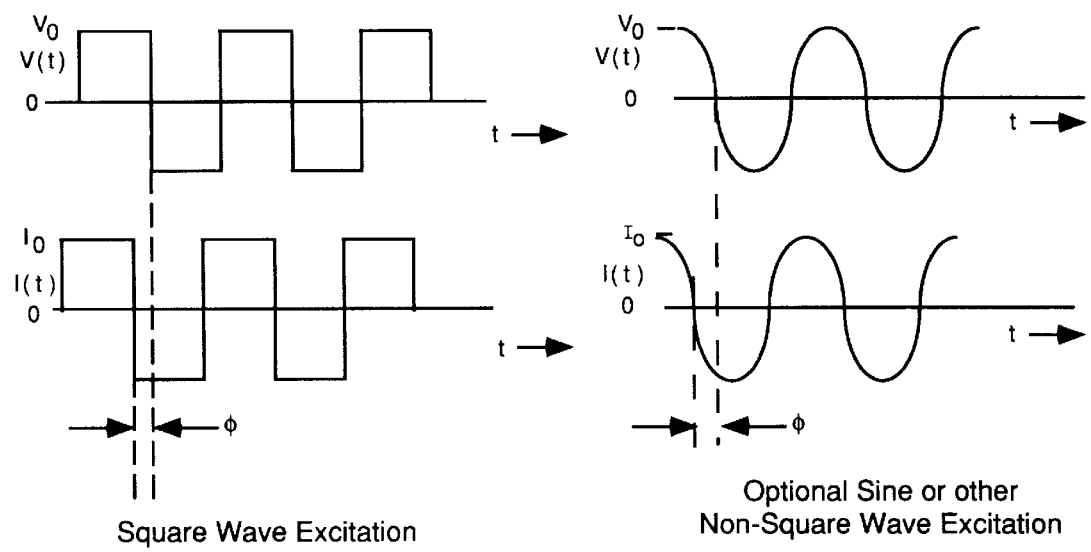
Fig. 6 PRIOR ART—High Frequency

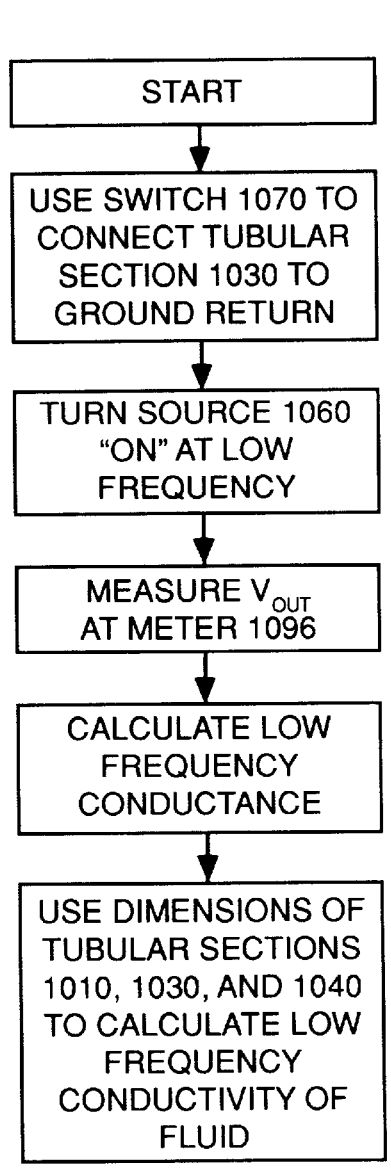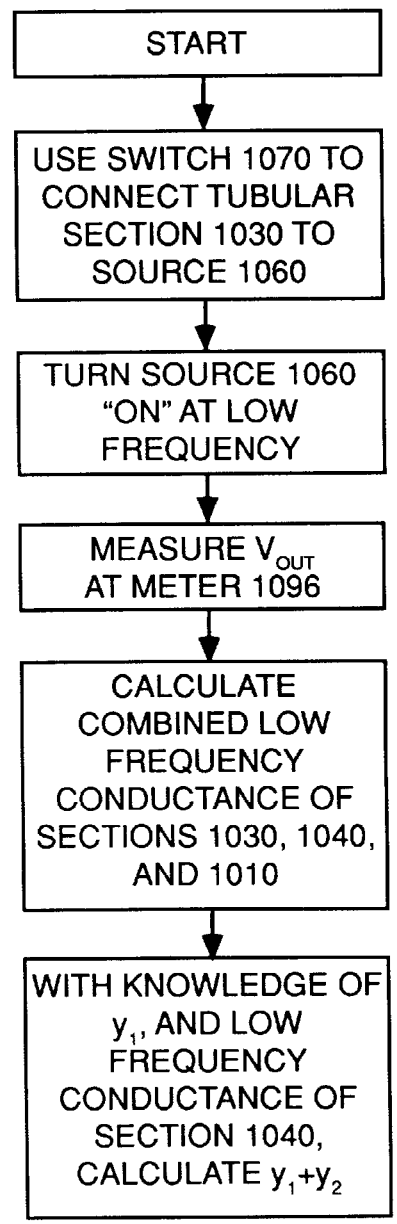
FIG. 12. LOW FREQUENCY CONDUCTANCE AND CONDUCTIVITY MEASUREMENT
FIG. 13. LOW FREQUENCY DEPTH MEASUREMENT

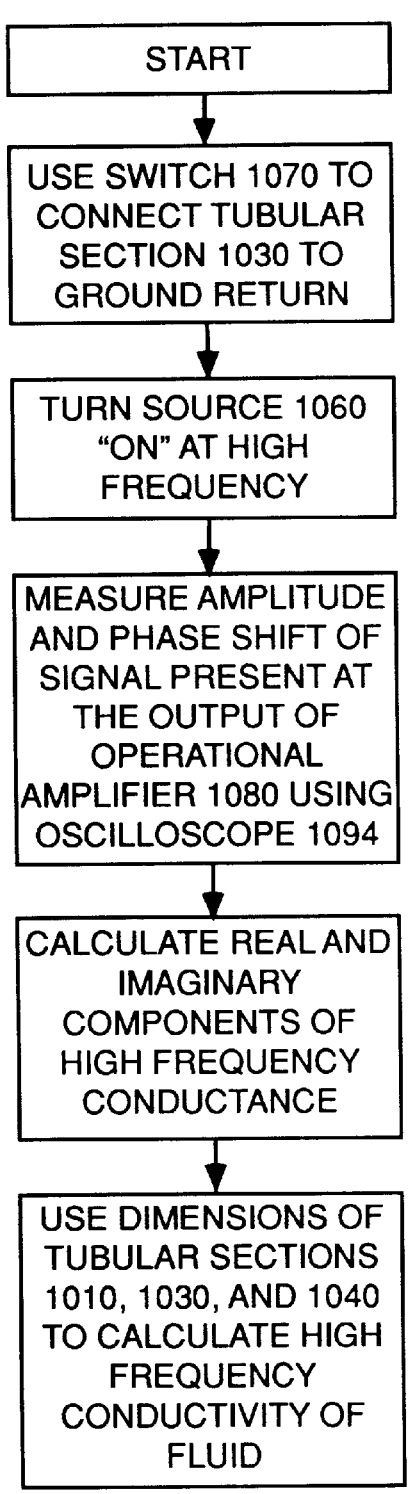
FIG. 14. HIGH FREQUENCY ADMITTANCE AND DIELECTRIC CONSTANT MEASUREMENT
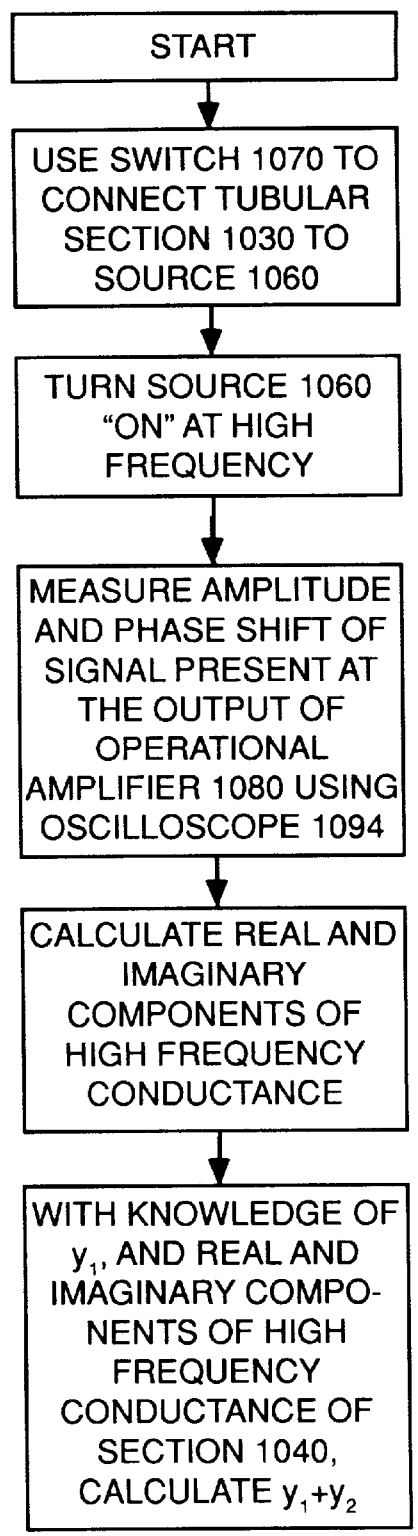
FIG. 15. HIGH FREQUENCY DEPTH MEASUREMENT

APPARATUS AND METHOD FOR COMBINING MEASUREMENT OF ELECTRICAL PROPERTIES AND DEPTH OF A FLUID

BACKGROUND—FIELD OF INVENTION

This invention relates to the measurement of physical and electronic properties, particularly to the measurement of electrical conductivity, dielectric constant, and depth of substances, namely fluids, fluid mixtures containing solid particles, and solids.

BACKGROUND—PRIOR-ART—FIGS. 1 TO 8—MEASUREMENT OF ELECTRICAL CONDUCTIVITY AND DIELECTRIC CONSTANT OF FLUIDS

Measurement of the electrical properties of fluids is frequently required in order to predict their performance in various situations. For example, the electrical conductivity of liquid toner is one of the determining factors of print quality in electrostatic printers. If the conductivity of the toner is higher or lower than an optimum value, the resultant optical density of prints will be low. In another example, the dielectric constant (permittivity or ability to concentrate flux in response to an applied electric field) of certain insulating oils determines their value as self-healing insulators in electrical transformers and capacitors.

Prior-art electrical conductivity and dielectric constant measurement methods and apparatus generally involve the use of "probes," such as that shown in FIG. 1. A typical probe is manufactured and sold by Scientifica, 340 Wall Street, Princeton, N.J. U.S.A. Such a probe comprises first and second electrodes: two tubes or cylinders. The length and outer diameter of outer tube 100 are typically 65 mm and 19 mm, respectively. The length and outer diameter of inner tube 110 are typically 45 mm and 15 mm, respectively. The wall thickness of the tubes is typically 1 mm. This leaves a gap between tubes of 1.0 mm. The tubes are held in place with respect to each another by insulating screws 120, typically made of a plastic material. Tubes 100 and 110 are connected to an external measuring apparatus (not shown) by wires 130 and 140, respectively.

Measurement of the conductivity and dielectric constant of a liquid toner solution will be used as an example to describe the use of this prior-art probe. Liquid toner is used to develop latent (non-visible) electrostatic images in electrostatic printers and copiers in well-known fashion. Liquid toner generally comprises a colloidal suspension of charged particles in a buffered solvent liquid. The charged particles are typically smaller than one micron in diameter. A net charge is imparted to each of the particles at the time of their manufacture. This process is well known to those skilled in the art of manufacture of liquid toners and will not be discussed further here.

The conductivity of the liquid toner solution depends upon at least two components: the ionic contribution due to the mobile particles, and the bulk, electronic conductivity of the solvent. The total conductivity is expressed as $\sigma_T = \sigma_i + \sigma_e$, where $\sigma_i$ is the ionic contribution and $\sigma_e$ is the electronic contribution. The mobile toner particles are also called the mobile ionic species to physically distinguish them from the electrons, or electronic species, which also conduct charge through the solution.

FIGS. 2 and 3 are simplified diagrams showing a planar adaptation of the prior-art conductivity probe of FIG. 1. The planar version of FIGS. 2 and 3 is used to more clearly show the motion of mobile particles in the space between the electrodes. Outer and inner cylinders 100 and 110 are replaced by first and second planar conductors 200 and 210 (200' and 210' in FIG. 3), respectively. For purposes of the present discussion the cylindrical and planar configurations are equivalent. The mobile ionic species comprising toner particles 240 (240') is assumed to have negative charge. FIG. 2 shows the distribution of charged, mobile particles immediately after the application of an externally-applied, electrical field E. Field E is identified as a vector to show the relative direction of motion of the mobile particles while the field is applied. FIG. 3 shows the distribution of charged, mobile particles after electrical field E has been applied for a very long time. The negatively charged, mobile particles are collected at the positively charged electrode. A source 220 (220') of electrical potential energy which can vary as a function of time, $V_0$, typically 5 volts, is connected between the electrodes to provide field E. An electrical current measuring meter 230 (230') is connected in series with source 220 and the electrodes.

Under the action of field vector E, negatively charged mobile particles 240 (240') move toward the positively charged electrode. FIG. 2 shows the motion of particles 240 shortly after potential V is applied to the probe. As the particles come into contact with first probe electrode 200 (200'), they attract a "mirror" charge of opposite sign (not shown) within the metal of the electrode. The movement of this mirror charge registers as the passage of current in current meter 230 (230'). If the direction of applied field E remains constant, negatively charged particles 240' will eventually congregate on positively charged electrode 200 (200'). When this happens, their contribution to the electrical current measured by meter 230(230') becomes zero. Any remaining indication of current is due to the motion of electronic charge or other ionic species through the bulk of the solvent liquid. Other ionic species are not considered here.

A plot of a step function of voltage with value $V_0$ and the resultant current I vs. time are shown in FIG. 4. When voltage V is first applied, mobile ionic particles 240 move toward first electrode 200, resulting in a nominally steady current, $I_0$. After a time, fewer mobile particles are available, and the measured current decreases as fewer particles impinge on first electrode 200. In some cases a smaller, residual current, $I^R$, will be measured. This residual current is due to electronic, or other ionic, processes, mentioned supra. The time required for the majority of mobile ionic particles to reach the first electrode is approximately 0.1 sec.

The contribution of the mobile species to conductivity is most easily measured using an alternating current (AC). If this is not the case and a direct current (DC) is applied to the probe, mobile species 240 (240') will all move to one electrode and remain there, as indicated in FIG. 3. In this case, they exhibit only a transient contribution to the total conductivity as they move. This transient current is shown in FIG. 4. Such a measurement is possible, but is more cumbersome and prone to error than an AC measurement.

In an AC measurement of conductivity, two frequency ranges are important: "low" frequencies, and "high" frequencies. Low frequencies are determined by the mobility of the ionic species, the applied electric potential, V, and the distance between the first and second electrodes. In the case of liquid toner and the above-mentioned cylindrical probe geometry, "low" frequencies are typically in the range of 10 to 30 Hz. The ionic conductivity of the toner is measured at a frequency which keeps all the mobile species in motion. The current and voltage waveforms typical at this frequency are shown in FIG. 5. In this case, the ionic population in the region between the first and second electrodes is never depleted and ionic current flow is limited by the mobile species' diffusion rate in the liquid. Hence the observed current does not decay during any half cycle of the AC. The quotient of the observed current, I, and the applied voltage, V, at any instant equals the electrical conductance between the two electrodes. Electrical conductance is a property which is measured by applying a potential to an electrical circuit and measuring the current through that circuit. Electrical conductivity is a physical property of a substance. This conductance can be directly related to the conductivity of the fluid in well-known ways, discussed infra. Measurement of the electronic contribution to conductivity can be performed in other ways, also discussed infra. Subtracting the electronic contribution from the total conductivity yields the ionic conductivity of the fluid. The ionic conductivity thus determined can be a useful measure of the mobile particle density in the toner.

If sufficiently "high" frequencies are applied to the probe, the ionic species will, on average, be unable to move to either electrode. Thus at these frequencies, the ionic contribution to the total measured conductivity is negligible. Typically, frequencies on the order of one kilohertz to one megahertz are applied to measure the admittance of the probe, and thus the electronic contribution to conductivity and the dielectric constant of the toner. At these frequencies, the capacitance of the probe becomes significant and the measured conductivity of the fluid between the electrodes is complex. The result of any algebraic operation on a "real" number yields another real number, except when the square root of a negative number is attempted. An "imaginary" number is defined as a number whose square is a negative number. Such numbers are useful in analyzing electrical circuits. A "complex" number contains both real and imaginary components. The current, I, through the probe "leads" the applied voltage, V by a phase angle $\phi$, as shown in FIG. 6. An equivalent circuit model for high frequency operation is given in FIG. 7. B represents the susceptance, or capacitive component, between the two electrodes. G represents the conductance, or resistive component, of the material between the two electrodes. The resulting admittance, which is in general complex, is the sum of the conductance of the conductive component and the susceptance of the capacitive component, $Y=G+jB$. The factor j is the square root of minus one. By noting the frequency, the phase angle $\phi$ between the applied AC voltage V, and the resultant current I, and with knowledge of the geometry of the probe, it is possible to determine the values of the real and imaginary components of the admittance. A vector plot of the complex admittance is shown in FIG. 8. The magnitude of the admittance $|Y|=|I_m|/|V_m|$, where m indicates the maximum value of the current and voltage waves. The conductance $G=|Y|\cos\phi$ is the electronic component of admittance. The capacitive susceptance $B=|Y|\sin\phi$. Conductance G and susceptance B are related to the electronic component of conductivity $\sigma e$ and dielectric constant $\in$ as follows.

$$\sigma_e=(d|Y|\cos\phi)/A, \text{ and } \in=(d|Y|\sin\phi/\omega A),$$

where d is the distance between electrodes, A is the area of the electrodes, and $\omega$ is $2\pi$ times the frequency of applied voltage V.

It is possible to use the electrical properties of a fluid to determine the depth of the fluid in a reservoir. While this prior-art apparatus and low and high-frequency measurements can determine the dielectric constant and ionic and electronic conductivities of a fluid, it can not also directly determine the depth of insertion of the probe into the fluid.

In order to use the prior art probe to determine the depth of a fluid, various calibration steps must be performed. These include independently measuring the ionic and electronic contributions to conductivity of the fluid, calibration of the probe and fluid together by partial immersion to known depths, noting values of conductivity vs. depth, and the like. If the conductivity of the fluid changes, a new calibration will be required. Such changes can occur if the mobile species are removed, as is the case with liquid toner, for example.

BACKGROUND—PRIOR-ART—FIG. 9— MEASUREMENT OF DEPTH OF A FLUID

Mechanical, electromechanical, optical, and sonic means are well known in the art of fluid level measurement and will not be discussed here. A means for measuring depth of a fluid by measuring resistance or capacitance between two electrodes is relevant to the present discussion.

FIG. 9 shows an apparatus for measuring the depth, h, of a liquid 900 in a reservoir. It is frequently necessary to measure the depth of fluids electronically when a remote indication is desired. Two electrodes 910 and 920, separated by a distance d, are immersed in liquid 900 and extend nearly to the bottom of reservoir 930. The electrical impedance between electrodes 910 and 920 is measured when reservoir 930 is full. The impedance measured as the liquid is drained from the reservoir will be inversely proportional to the level, h, of liquid 900 in the reservoir. However the impedance vs. depth will not be known unless the system has previously been calibrated. Results will be different for liquids with different electrical properties. If the conductivity of liquid 900 is known, the expected resistance as a function of the depth of the liquid can be calculated. Capacitance measurements can be used similarly to measure the depth of fluid in the reservoir. Whether capacitance or resistance measurements are used depends upon the nature of the liquid.

An example of a capacitive probe which is intended to measure depth of insertion of a probe into a liquid is the model LV5202-Y0-Z0, sold by Omega Engineering, Inc., One Omega Drive, Stamford, Conn. 06907, U.S.A. In order to determine depth of insertion, this probe requires either calibration, or an assumption as to the value of the dielectric constant and conductivity of the liquid.

Measurement of fluid depth by this method requires calibration, either through prior knowledge of the electrical properties of the fluid, or by filling and then at least partially draining the reservoir, noting at least two values of impedance at two different depths, h, then interpolating measurements for other depths. It is not possible to directly measure the depth of insertion of a probe in a liquid by this measurement without prior calibration. This requirement is a distinct disadvantage when the reservoir is re-filled with liquids which have different properties, or whose properties change over time.

OBJECTS AND ADVANTAGES

Accordingly several objects and advantages of the present invention are to provide a convenient means for measuring the real and imaginary components of the electrical admittance of a probe in a fluid. Further objects are to provide means for measurement of the conductivity and susceptibility of a fluid, the depth of insertion of a probe into a fluid, to combine the measurements of admittance and depth of immersion of the probe into the fluid, to combine the admittance and depth measurements in a way which does not require calibration of the apparatus for each different fluid measured, and to provide means for measuring the depth of a fluid whose properties change over time.

Additional objects and advantages will become apparent from a consideration of the drawings and ensuing description thereof.

SUMMARY

In accordance with the present invention, a simple probe apparatus is provided which measures electrical admittance of a fluid while also measuring the depth of insertion of the apparatus into the fluid. The depth measurement is made without a priori calibration of the apparatus. The probe can be inserted in different fluids with differing properties, and whose properties change over time, and still accurately report the electrical properties of the fluid and the depth of insertion of the probe. All measurements can be made from first principles and a knowledge of the geometry of the probe apparatus.

The instant probe comprises two interconnected sections which share a common, inner electrode. Concentric with the inner electrode are two outer electrodes, one mounted below the other. The lower of these is of a known, relatively short axial extent. It is used, in conjunction with the inner electrode, to measure the properties of the fluid. The upper and lower electrodes together are used to measure the depth of the fluid.

BRIEF DESCRIPTIONOF THE DRAWINGS

FIG. 1 is a schematic drawing of a prior-art liquid conductivity measurement probe.

FIG. 2 is a schematic diagram of a prior-art electrical circuit comprising a source of known electrical potential, probe electrodes, current meter, and mobile ionic species.

FIG. 3 is a schematic diagram showing the elements of FIG. 2 at a later time.

FIG. 4 shows graphical representations of voltage applied to the prior-art probe of FIG. 1 and the resultant current, both as a function of time.

FIG. 5 is a plot of "low frequency" applied AC voltage and the resulting current through a prior-art probe similar to that of FIG. 1.

FIG. 6 is a plot of "high frequency" applied AC voltage and the resulting current through a prior-art probe similar to that of FIG. 1.

Figure 7:
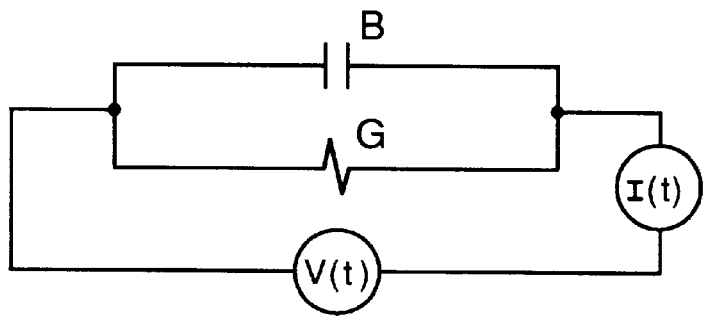
FIG. 7 is a schematic, equivalent circuit of a prior-art probe similar to that of FIG. 1 immersed in a fluid.

FIG. 12. is a flow chart showing the steps in measurement of the low frequency conductance of the probe circuit and the conductivity of the fluid or other medium under study.

FIG. 13. is a flow chart showing the steps in determining depth of the fluid or other medium under study when the instant system is operated at a low frequency.

FIG. 14. is a flow chart showing the steps in determining the high frequency admittance of the probe circuit and the dielectric constant of the fluid or other medium under study.

FIG. 15. is a flow chart showing the steps in determining depth of the fluid or other medium under study using a high frequency potential.

DRAWING REFERENCE NUMERALS

Figure 9:
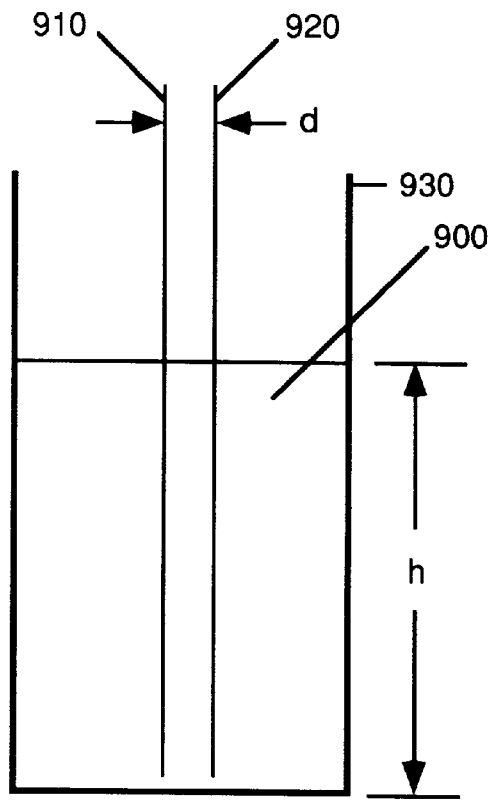
FIG. 9 is a schematic diagram of prior-art apparatus for measurement of depth of a liquid.
Figure 10:
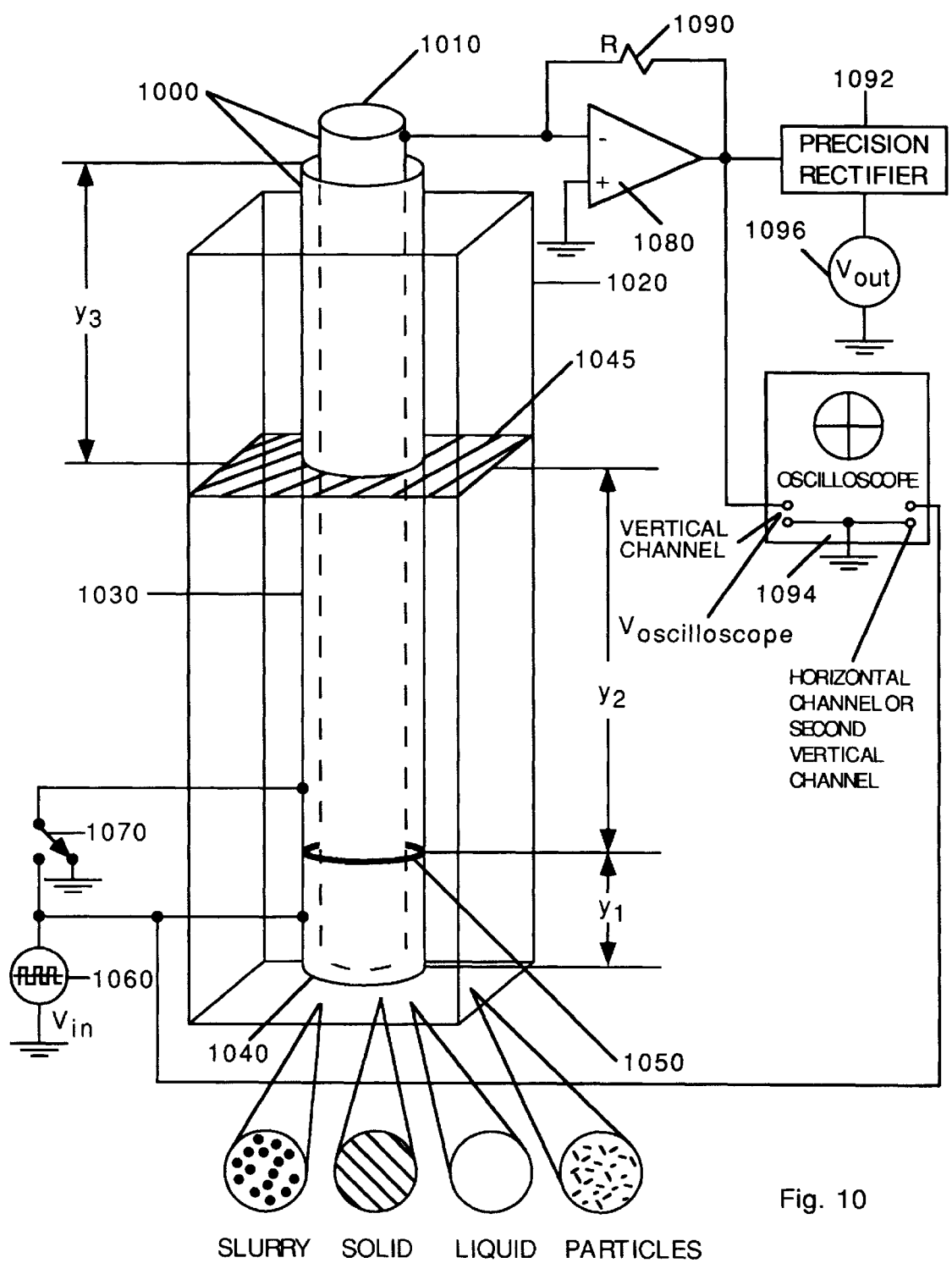
FIG. 10 is a drawing of a probe according to the present invention, showing the combination of impedance and depth measurements.
Figure 11:
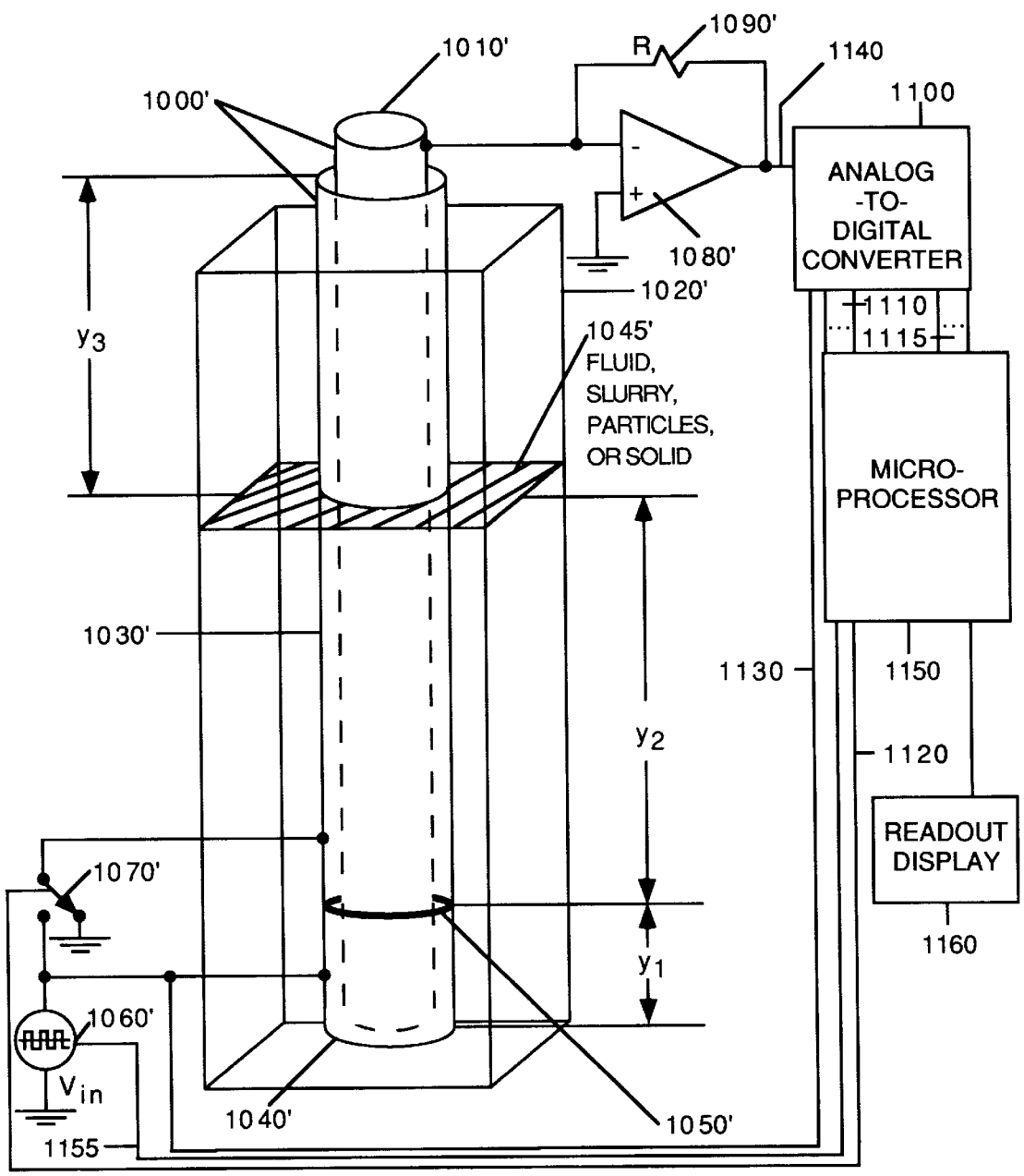
FIG. 11 is a drawing of an alternate embodiment of the present system.

FIG. 1—Prior-Art
   100 Outer tube
   110 Inner tube
   120 Screw
   130 Connecting wire
   140 Connecting wire
FIG. 2—Prior-Art
   200 First electrode
   210 Second electrode
   220 Potential source
   230 Current meter
FIG. 3—Prior-Art
   200 First electrode
   210 Second electrode
   220 Potential source
   230 Current meter
FIG. 9—Prior-Art
   900 Liquid
   910 First electrode
   920 Second electrode
   930 Reservoir
FIG. 10—Preferred Embodiment of the Present System
   1000 Probe assembly
   1010 Innertube
   1020 Reservoir
   1030 Upper, outer tubular section
   1040 Lower, outer tubular section
   1045 Fluid
   1050 Annulus
   1060 Voltage source
   1070 Switch
   1080 Operational amplifier
   1090 Feedback resistor
   1092 Precision rectifier
   1094 Oscilloscope
   1096 Voltmeter
FIG. 11—Alernate Embodiment of the Present System
   1000'Probe assembly
   1010' Innertube
   1020' Reservoir
   1030' Upper, outer tubular section
   1040' Lower, outer tubular section
   1045' Fluid
   1050' Annulus
   1060' Voltage source
   1070' Switch
   1080' Operational amplifier
   1090' Feedback resistor
   1100 Analog-to-digital converter
   1110 Multiple control lines
   1115 bMultiple signal lines
   1120 Control line
   1130 ADC signal input line 1140 ADC signal input line
1150 Microprocessor
1155 Control line
1160 Readout display

IMPEDANCE AND DEPTH MEASUREMENT SYSTEM, PREFERRED EMBODIMENT—FIG. 10—DESCRIPTION

A preferred embodiment of the present system as applied to measurement of the electrical properties and depth of liquid toner is shown in FIG. 10. The instant system comprises a novel combination of two probes, one of which measures the electrical admittance of the liquid, while the second, in combination with the first, measures the depth of insertion of the probes into the liquid. With a knowledge of the electrical properties of the liquid obtained fiom the first probe, the second probe is used to measure the depth of insertion of both probes into the liquid.

A reservoir 1020 contains a fluid 1045 (only the surface of the fluid is shown for clarity) whose admittance and height in reservoir 1020 are to be measured. Reservoir 1020 can be, for example, a bottle, a drum, an open or closed reservoir, and the like. Probe assembly 1000, containing the two probes mentioned supra, preferably comprises three tubular sections which are inserted into reservoir 1020. An inner tube 1010 is common to both probes. Outer tubular section 1040 and inner tube 1010 comprise a first probe, while outer tubular section 1030 and inner tube 1010 comprise a second probe. Inner tube 1010 is continuous over its length and extends nominally from the bottom to the top of reservoir 1020. Outer tubes 1030 and 1040 are connected mechanically but are electrically disjointed or insulated from one-another. The outside diameter of inner tube 1010 is preferably 15 mm, and outer tubular sections 1030 and 1040 typically have an inside diameter of 17 mm. Outer tubular sections 1030 and 1040 are separated by an electrically insulating annulus 1050, preferably made of a plastic material which is not attacked by the fluid 1045. Annulus 1050 typically has an axial extent of 1 mm. The combined lengths of tubular sections 1030 and 1040 and annulus 1050 approximately equal the length of inner tube 1010. The wall thickness of all three tubular sections is typically 1 mm. The fluid under study 1045 is free to flow in the space between the inner and outer tubular sections.

Annulus 1050 preferably rigidly joins tubular sections 1030 and 1040, and does not interfere with the flow of fluid in the spaces between the inner and outer tubular sections.

The axial extent of lower, outer tubular section $y_1$, 1040, is typically 2 cm, while the axial extent of upper, outer tubular section, $Y_2$ 1030 is typically 18 cm. AC voltage source 1060, operating with reference to ground potential, is connected to lower, outer tubular section 1040. A switch 1070 is a SPDT (Single Pole, Double Throw) switch which connects outer tubular section 1030 either to source 1060 or to ground return. Switch 1070 can be either a mechanical switch or a solid-state switch activated by external mechanical or electrical circuit means (not shown).

Inner tubular section 1010 is connected to an inverting input of an operational amplifier 1080. The non-inverting input of amplifier 1080 is connected to ground potential. A feedback resistor $R_f$ 1090 determines the gain of amplifier 1080. The output of amplifier 1080 is connected to a precision rectifier 1092 and to an external measuring device, preferably an oscilloscope 1094. A precision rectifier 1092 rectifies the signal present at the output of operational amplifier 1080. The output of precision rectifier 1092 is connected to an indicating device such as voltmeter 1096.

For other measurement purposes, fluid 1045 can comprise, as indicated, a liquid, a solid, a collection of solid particles, a slurry of solid particles in a liquid, and the like.

CONDUCTIVITY MEASUREMENT—LOW FREQUENCY—FIG. 10

The ionic and electronic conductivities are measured separately using two different frequencies, as described supra. Assume that the fluid level in reservoir 1020 is always greater than $y_1$. Fringing electrical fields are neglected in this discussion. To measure the conductivity of the fluid in reservoir 1020 using a low frequency, lower tubular section 1040 is connected to voltage source 1060. Upper tubular section 1030 is connected to ground potential. A low frequency voltage V, nominally ±2.5 volts at a frequency of 30 Hz, is applied by source 1060 to tubular section 1040. A resulting current I will flow through fluid 1045 to the virtual ground at the input of amplifier 1080. Precision rectifier 1092 rectifies the voltage at the output of amplifier 1080. Voltmeter 1096 indicates the maximum value of this output voltage. The maximum current flowing through the fluid in the space between tubular section 1040 and inner tube 1010 is equal to the peak amplitude of $V_{in}$, $V_{in}$ peak, multiplied by the conductance of the circuit comprising tubes 1010 and 1040, and fluid 1045 in the space between the two sections. The output of amplifier 1080 is equal to I times $R_f$, where $R_f$ is the resistance of feedback resistor 1090. The conductance is measured by dividing the output voltage $V_{out}$ by the product of the peak value of the applied potential of source 1060 and the feedback resistor 1090. Thus the measured conductance of the fluid in the inter-tubular region between section 1040 and tube 1010 is $G = V_{out}/(V_{in\ peak} R_f)$.

The conductivity of the fluid in the inter-tubular space is equal to: $\sigma = Gd/A$, where d is the radial distance between the inner and outer tubular sections, A is the area of the above-mentioned inter-tubular space, and G is the measured conductance of the probe. Substituting the measured value determined supra for G, and geometric dimensions A and d of probe assembly 1000 above yields the total conductivity of the fluid $\sigma = 6 \times 10^{-3} \times V_{out}/(V_{in\ peak} R_f y_1)$. Each of the variables in this equation is known or can be measured without prior calibration of probe 1000.

CONDUCTIVITY MEASUREMENT—HIGH FREQUENCY—FIG. 10

To measure the high-frequency component of conductivity, lower tubular section 1040 is connected to voltage source 1060. Upper tubular section 1030 is connected to ground potential. Assume that lower tubular section 1040 is completely immersed in fluid 1045. A high frequency voltage V, nominally ±2.5 volts at a frequency of 100 kHz, is applied by source 1060 to tubular section 1040. A resulting current I will flow through the liquid toner to the virtual ground at the input of amplifier 1080. The output of amplifier 1080 is equal to I $R_f$, where $R_f$ is the resistance of feedback resistor 1090. Thus I is equal to the amplitude of the voltage indicated on the vertical axis of oscilloscope 1094, divided by $R_f$. The horizontal channel of oscilloscope 1094 is triggered by voltage $V_{in}$. This trigger signal can be supplied directly to the horizontal channel, or indirectly through a second vertical channel. Thus oscilloscope 1094 also indicates the phase shift, φ, between $V_{in}$ and I, in well-known fashion. The current flowing through the liquid toner in the space between tubular section 1040 and inner tube 1010 is equal to the amplitude of $V_{in}$ and divided by the admittance of the liquid toner in the space between the two sections. At this frequency the admittance is complex, i.e. it contains a real and an imaginary component. Because it is complex, it is represented here by bold print. Thus, referring to FIG. 8, as above, the magnitude of the measured admittance of the liquid toner in the inter-tubular region between section 1040 and tube 1010 is $|Y|=V_{oscilloscope}/(V_{in\ peak} R_f)$. The non-ionic conductance $G=|Y| \cos \phi$. The capacitive susceptance $B=|Y| \cos \phi$. $\phi$ is the angular displacement between $V_{oscilloscope}$ and $V_{in\ peak}$.

As described supra, once the admittance is known it is possible to calculate the conductivity of the fluid through geometric considerations. The high-frequency, non-ionic component of conductivity of the liquid toner in the inter-tubular space is equal to $\sigma_e=(d|Y| \cos \phi)/A$, where d is the radial distance between the inner and outer tubular sections, A is the area of the above-mentioned inter-tubular space, and $|Y|$ is the magnitude of the measured admittance of the probe.

DIELECTRIC CONSTANT—FIG. 10

The instant circuit comprises a capacitance in parallel connection with a conductance, similar to that shown in FIG. 7. The susceptance $B=\omega C=2\pi f C$, where f is the frequency of the applied potential and C is the capacitance of the capacitor. The capacitance of a capacitor is given by $C=\in A/d$. As above, the measured value for B is $|Y| \cos \phi$. Substituting and rearranging these equations, it is seen that the dielectric constant $\in$ of the liquid toner in the inter-tubular space is equal to $d|Y| \sin \phi/\omega A$, where d is the distance between electrodes, A is the area of the electrodes, and $\omega$ is $2\pi$ times the frequency of applied voltage $V_{in}$. $|Y|$ and $\phi$ are measured as described supra. d and A are known from the dimensions of probe sections 1010 and 1040, and $\omega$ is a known parameter of source 1060.

DEPTH OF INSERTION OF THE COMBINED PROBE ASSEMBLY—FIG. 10

To measure the depth of insertion of the probe in fluid 1045, the following measurements are noted. With switch 1070 connected to ground, the measured admittance Y for the lower portion of probe 1000 is proportional to distance $y_1$. With switch 1070 connected to upper section 1030 of probe 1000, the measured admittance Y is proportional to $y_1+y_2$. Thus only two measurements are required to determine the depth of insertion of probe 1000 in fluid 1045. Writing the total admittance as a function of y, $y1+y2=y_1Y$ (measured at a depth of $y_1+y_2$)/Y(determined for $y_1$ only). This measurement can be made at low frequencies, in which case only the real, ionic conductivity is measured. Alternatively the measurement can be made at high frequencies, in which case Y is complex. Both measurements yield the same result. The high frequency measurement requires more computation than the low frequency measurement.

ALTERNATIVE ELECTRONICS CONFIGURATION—FIG. 11

As shown in FIG. 11, precision rectifier 1092, voltmeter 1096, and oscilloscope 1094 of FIG. 10 can be replaced by an analog-to-digital converter (ADC) 1100, a microprocessor 1150, and a readout display 1160. In this embodiment, microprocessor 1150 controls the action of source 1060' via control line 1155, i.e. microprocessor 1150 selects the voltage amplitude, frequency, and waveform produced by source 1060'. ADC 1100 receives inputs from source 1060' and operational amplifier 1080' via lines 1130 and 1140. Signals on these lines are interpreted in a manner similar to that in FIG. 10. Microprocessor 1150 includes a PROM (Programmable Read-Only Memory) to control its functions so that it provides control signals to ADC 1100 via control lines 1110. This control of a microprocessor by a PROM is well understood by those familiar with the art of microprocessor design. The PROM is programmed according to the flowcharts of FIGS. 12 to 15, discussed below. The ADC output is communicated to microprocessor 1150 via signal lines 1115. Microprocessor 1150 performs the required calculations according to the algorithms described supra and presents the results on readout display 1160. Readout display 1160 is preferably a computer screen, but can also be a liquid crystal display, a light-emitting diode display, a printer, or the like. The results can be displayed numerically or graphically.

LOW FREQUENCY CONDUCTANCE AND CONDUCTIVITY MEASUREMENT—FIG. 12-Flow Chart

In the following discussion of flow charts, reference is also made to FIG. 10.

As shown in FIG. 12, after the START, the PROM causes switch 1070 first to connect tubular section 1040 to ground potential.

Source 1060 is then turned "ON" at a low frequency, nominally 20 Hz.

Next, a value is chosen for feedback resistor 1090 such that a reliable reading is given on voltmeter 1120. The measured admittance Y is given by Y=I/V, where I is the current flowing in fluid 1045 between electrodes 1040 and 1010. I is determined from the output of voltmeter 1060 and resistor 1090 in well-known fashion. $I=V_{out}/R_f$. Thus $Y=V_{out}/(V_{in\ peak} R_f)$. All parameters in this equation are known or can be directly measured. Further, the conductance in the low frequency case can be assumed to equal the admittance since the imaginary component of admittance is nearly zero. This was one of the determining factors in selecting the frequency in this case, as described supra. Hence $G=V_{out}/(V_{in\ peak} R_f)$.

Next, with the knowledge of the admittance, the low-frequency conductivity of fluid 1045 is calculated from geometrical considerations. The conductance of a fluid between electrodes 1040 and 1010 is defined as $G=\sigma A/d$, where $\sigma$ is the conductivity of the fluid, A is the area of the region through which the ionic current flows, and d is the spacing between the electrodes. Rearranging this equation gives $\sigma=G\ d/A$.

In one preferred embodiment of the instant invention, d equals 0.1 cm. The diameter of inner tube 1010, D, is 1.5 cm. The axial extent, h, of electrode 1040 is 2 cm. Thus the area between electrodes 1040 and 1010, $\pi D^2 h/4=3.53$ cm$^2$. If $R_f=10^9$ ohms, $V_{out}=5$ volts and $V_{in\ peak}=2.5$ volts, then $$\sigma=A\ (V_{out}/(V_{in\ peak}\ R_f))/d=4.7\times 10^{-8}\ \text{mho/cm}.$$

LOW FREQUENCY DEPTH MEASUREMENT—FIG. 13-Flow Chart

The steps of FIG. 13 are used to measure the depth, $Y_1+Y_2$, of fluid 1045.

After START, switch 1070 connects tube 1030 to voltage source 1060.

Next, source 1060 is turned "ON" at a low frequency and $V_{out}$ is measured using meter 1120. The combined, low-frequency conductance of the fluid between tubes 1030 and

1040 connected in parallel, and tube 1010, is proportional to the axial dimension $Y_1+Y_2$, as described supra. Thus G(determined for $y_1$)/$y_1$=G(determined for $Y_1+Y_2$)/($Y_1+Y_2$). Solving for $Y_1+Y_2$ gives the desired result: $Y_1+Y_2$= G(determined for $Y_1+Y_2$) $y_1$/G(determined for $y_1$).

HIGH FREQUENCY ADMITTANCE AND DIELECTRIC CONSTANT MEASUREMENT—FIG. 14-Flow Chart In the measurement indicated in FIG. 14, after START, switch 1070 first connects tube 1030 to ground potential.

Next, source 1060 is turned "ON" at a high frequency, as determined supra.

Next, oscilloscope 1094 is used to measure the amplitude and phase shift of the voltage present at the output of amplifier 1080. It is a requirement that amplifier 1080 does not introduce additional phase shift, or that its phase shift is a known value which can be subtracted from the final measurement.

Next, the total admittance is measured as follows. Complex values, i.e. those with a real and an imaginary component are shown in bold type. Y=I/V, where Y is the complex admittance, I is the peak amplitude of current through fluid 1045, and V is the peak amplitude of voltage from source 1060. As above, the magnitude of current $|I|=V_{peak}/(V_{in\ peak} R_f)$. Thus the magnitude of the admittance $|Y|$ equals $V_{oscilloscope\ peak}/(V_{in\ peak} R_f)$.

Figure 8:
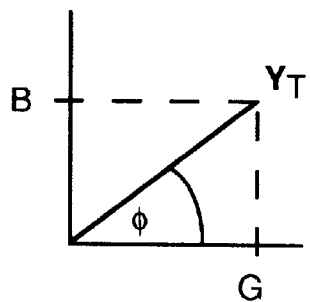
FIG. 8 is a plot of the electrical admittance measured by the circuit of FIG. 7.

Next, the phase angle between the voltage of source 1060 and the output of amplifier 1080 is measured in well-known fashion using oscilloscope 1110. Reference to FIG. 8 shows the relation between the real and imaginary components of admittance Y. $\phi$ is the measured phase angle, G is the conductance and B is the susceptance of the circuit comprising tubes 1010, 1040 and fluid 1045. j is the square root of −1. Thus $G=|Y|\cos\phi$ and $B=|Y|\sin\phi$.

HIGH FREQUENCY DEPTH MEASUREMENT—FIG. 15-Flow Chart

As for the low-frequency case, separating the real and imaginary components as above, $Y_1+Y_2$=G(determined for $Y_1+Y_2$) $y_1$/G(determined for $y_1$) or $Y_1+Y_2$=B(determined for $Y_1+Y_2$) $y_1$/B(determined for $y_1$).

The operations of FIGS. 12 through 15 are selected by varying the frequency of source 1060, the position of switch 1070, and the measurement method. The indication of voltmeter 1096 is adequate for the low frequency measurements, while the indication of oscilloscope 1094 is required for the high frequency measurements.

SUMMARY RAMIFICATIONS, AND SCOPE

It is thus seen that the present system combines a method for determining the electrical properties of a fluid and a method for measuring the depth of the fluid. Low frequency and high frequency measurements are used to separate the ionic and electronic conductivity, and to measure the dielectric constant of the fluid. Either a low frequency or a high frequency measurement can be used to determine the depth of the fluid. The novel combination of these two measurements provides a probe assembly which can be used to measure the depth of a liquid without a priori knowledge of the fluid's electrical properties. Further, the depth of a fluid whose electrical properties change with time can be accurately measured since the fluid's electrical properties are measured as part of the depth measurement. While the present system employs elements which are individually well known to those skilled in the separate arts of electronics, mechanical engineering, and materials properties, it combines elements from these fields in a novel way which produces new results not heretofore discovered. Although the invention has been described with specific components and parameters, these can be varied in many ways without departing from its scope.

For example, source 1060 supplies a square-wave voltage, it is possible to use Fourier analysis of the resulting waveforms to simultaneously analyze the low-and high-frequency components of behavior of the circuit comprising fluid 1045 and either of the combinations of tubes 1010, 1030 and 1040.

Instead of a single source 1060 which is connected to tube 1030 via switch 1070, a second electrical potential source, not shown, can be used to provide a signal to outer tubular section 1030. The second source is turned on when it is desired to know the total admittance of the probe comprising both of tubes 1030 and 1040.

Instead of stainless steel, probe assembly 1000 can be made of aluminum, or metalcoated glass or plastic, or other materials. Sections 1030 and 1040 can be made of dissimilar metallic conductors. Instead of a tube, inner tube 1010 can be a solid rod. Alternatively, instead of being a passive tube, inner tube 1010 can be a conduit in a pumping system used to move a fluid of any kind from one location to another. In a further option a heater or cooling means can be positioned inside tube 1010 to heat or cool the instant measuring apparatus if required.

If fluid 1045 is pumped at a known rate, axially in the space between inner tube 1010 and outer tubes 1030 and 1040, the admittance of fluid 1045 can be measured as a function of shear rate.

Instead of having a circular cross-section, tubes 1010, 1030, and 1040 can have square, elliptical, or irregular cross-sectional shapes.

Instead of dividing the outer tubular sections into two separately actuated conductors, the outer tubular section can be one piece while the inner tubular conductor 1010 is divided into two pieces. The outer tubular section is connected to operational amplifier 1080, while the inner tubular sections are connected to source 1060 and switch 1070.

Instead of tubes, rods, spheres, plates, disks and other geometries can be combined in various ways which perform the same measurement. For example, two parallel rods are be placed in proximity. One rod is continuous over a length comparable to that of tube 1010 in FIG. 10. This rod is connected to the input of amplifier 1080. The other rod comprises two sections, mechanically connected but electrically insulated from each other. One section is of a length comparable to tubular section 1040 (FIG. 10). The other section is comparable to the length of tubular section 1030 (FIG. 10). The longer and shorter of these are connected to switch 1070 and source 1060 (FIG. 10), respectively.

The size (diameter and length) of probe assembly 1000 can vary from large (many meters in axial extent) to small (only a few millimeters in extent). Although shown close together, the separation between outer tubular sections 1030 and 1040 can be as large as practical considerations permit. The diameters of the inner and outer sections are limited only by practical considerations in making the measurements described.

The function of annulus 1050 can be served by using insulating spokes, not shown, to support outer tubular sections 1030 and 1040 on inner tube 1010. In this case, annulus 1010 can be removed. Alternatively, the above-mentioned insulating spokes, not shown, can be used to support outer tubes 1030 and 1040 from without their circumference by another means, not shown.

Switch 1070 can be electronic (solid-state), or mechanical. Instead of a single SPDT switch, two SPST switches can be used.

Precision rectifier 1092, voltmeter 1096, and oscilloscope 1094 can be replaced by other electronic circuitry, such as an analog-todigital converter and the like. Instead of visual readouts, the analog-to-digital converter circuitry can provide information to computer software programs for analysis and display.

Voltage source 1060 can be used to supply a square wave, a sine wave, or other waveform. The wave's amplitude and frequency can be held constant during a measurement, or varied during a measurement if that is advantageous. Different frequencies can be applied to the two probes, if desired.

Although reservoir 1020 is shown as "open," it can also be closed. Reservoir can be a metal drum, a plastic or glass bottle, an earthen hole or any other fluid reservoir. Fluid 1045 can be under positive or negative pressure with respect to its immediate environment. Fluid 1045 can be transparent, translucent, or opaque. In lieu of toner liquid fluid 1045 can comprise any conductive gas, a liquid, or a slurry of particles in a liquid or a gas. Also a solid can be measured instead of a fluid. The solid can be liquefied, melted or dissolved, then poured into reservoir 1020 and allowed to solidify. Alternatively, the solid can be machined to a shape similar to the interelectrode space, and electrodes applied to its inner and outer surfaces. A thixotropic substance can be forced into the space between electrodes.

Although tubular sections 1010, 1030, and 1040 are preferably rigidly mounted with respect to one-another, it is possible to mount one or more of them movably with respect to the others.

Accordingly the scope of this invention should be determined, not by the embodiments illustrated, but by the appended claims and their legal equivalents.

I claim:

1. A measurement system, comprising:
   a. potential source means with a ground return,
   b. a plurality of electrically conductive sections, said sections being electrically separate,
   c. connecting means for connecting a first of said sections to said potential source means, said first section having predetermined physical dimensions,
   d. potential switching means for selectively connecting a second of said sections to either said potential source means or to said ground return,
   e. electrical current measuring means, and
   f. connecting means for connecting one of said sections to said electrical current measuring means.

2. The system of claim 1 wherein said sections are tubular.

3. The system of claim 1 wherein said sections are concentrically disposed.

4. The system of claim 1 wherein said potential source means is a sine wave source.

5. The system of claim 1 wherein said potential source means is arranged to produce a potential having a non-sinusoidal waveform.

6. The system of claim 1 wherein said potential switching means is a mechanical switch.

7. The system of claim 1 wherein potential switching means is a solid-state switch.

8. The system of claim 1 wherein the physical dimensions of said second section are predetermined.

9. A measurement system, comprising:
   a. potential source with a ground return,
   b. a plurality of electrically conductive sections, said sections being electrically separate,
   c. a first switch for connecting a first of said sections to said potential source, said first section having predetermined physical dimensions,
   d. a second switch for selectively connecting a second of said sections to either said potential source or to said ground return,
   e. an electrical current measuring circuit, and
   f. a switch for connecting one of said sections to said electrical current measuring circuit.

10. The system of claim 9 wherein said sections are tubular.

11. The system of claim 9 wherein said sections are concentrically disposed.

12. The system of claim 9 wherein said potential source is a sine wave source.

13. The system of claim 9 wherein said potential source is arranged to produce a potential having a non-sinusoidal waveform.

14. The system of claim 9 wherein potential switch is a mechanical switch.

15. The system of claim 9 wherein potential switch is a solid-state switch.

16. The system of claim 9 wherein the physical dimensions of said second section are predetermined.

17. A measurement method, comprising
   a. providing a potential source with a ground return,
   b. providing a plurality of electrically conductive sections, said sections being electrically separate,
   c. connecting a first of said sections to said potential source, said first section having predetermined physical dimensions,
   d. selectively connecting a second of said sections to either said potential source or to said ground return,
   e. providing an electrical current measuring circuit, and
   f. connecting one of said sections to said electrical current measuring circuit.

18. The method of claim 17 wherein said sections are tubular.

19. The method of claim 17 wherein said sections are concentrically disposed.

20. The method of claim 17 wherein said potential source is a sine wave source.

21. The method of claim 17 wherein said potential source is arranged to produce a potential having a non-sinusoidal waveform.

22. The method of claim 17 wherein said selectively connecting is performed with a mechanical switch.

23. The method of claim 17 wherein said selectively connecting is performed with a solid-state switch.

24. The method of claim 17 wherein the physical dimensions of said second section are predetermined.

* * * * *